US009383311B2

(12) United States Patent
Ran et al.

(10) Patent No.: US 9,383,311 B2
(45) Date of Patent: *Jul. 5, 2016

(54) NON-SCANNING SPR SYSTEM

(71) Applicant: Bio-Rad Laboratories Inc., Hercules, CA (US)

(72) Inventors: Boaz Ran, Haifa (IL); Itay Barak, Haifa (IL)

(73) Assignee: Bio-Rad Laboratories Inc., Hercules, CA (US)

( * ) Notice: Subject to any disclaimer, the term of this patent is extended or adjusted under 35 U.S.C. 154(b) by 272 days.

This patent is subject to a terminal disclaimer.

(21) Appl. No.: 14/013,068

(22) Filed: Aug. 29, 2013

(65) Prior Publication Data

US 2013/0344623 A1 Dec. 26, 2013

Related U.S. Application Data

(63) Continuation of application No. 12/762,338, filed on Apr. 18, 2010, now Pat. No. 8,530,243.

(60) Provisional application No. 61/170,679, filed on Apr. 20, 2009.

(51) Int. Cl.
*G01N 21/00* (2006.01)
*G01N 21/552* (2014.01)
(Continued)

(52) U.S. Cl.
CPC .............. *G01N 21/553* (2013.01); *G02B 3/005* (2013.01); *G02B 5/008* (2013.01)

(58) Field of Classification Search
CPC . G01N 21/553; G01N 21/648; G01N 21/658; G01N 21/552; G01N 21/253; G01N 2021/058; G01N 2021/6419; G01N 2021/6421; G01N 2021/212; G01N 2021/655; G01N 2021/258
See application file for complete search history.

(56) References Cited

U.S. PATENT DOCUMENTS

| 4,767,719 A | 8/1988 | Finlan |
| 4,889,427 A | 12/1989 | Van Veen et al. |

(Continued)

FOREIGN PATENT DOCUMENTS

| EP | 0286195 | 10/1988 |
| EP | 0341928 | 11/1989 |

(Continued)

OTHER PUBLICATIONS

Applicant-Initiated Interview Summary Dated Feb. 26, 2013 From the US Patent and Trademark Office Re. U.S. Appl. No. 12/762,338.
(Continued)

*Primary Examiner* — Yelena G Gakh

(57) ABSTRACT

A system for measuring an evanescent wave phenomenon at total internal reflection, the system comprising:
a) a sensing surface comprising a plurality of areas of interest;
b) an illumination sub-system comprising a light source, which illuminates each area of interest on the sensing surface over a range of angles of incidence;
c) a detector which responds differently to an intensity of light received by it at different locations; and
d) projection optics comprising primary optics and a plurality of secondary elements, the primary optics projecting an image of the illuminated sensing surface onto the secondary elements, which project their received light onto the detector in such a way that it is possible to determine, from the response of the detector, how much light is reflected from each area of interest, as a function of angle of incidence over the range of angles for that area.

19 Claims, 9 Drawing Sheets

(51) Int. Cl.
*G02B 3/00* (2006.01)
*G02B 5/00* (2006.01)

(56) References Cited

U.S. PATENT DOCUMENTS

| | | | |
|---|---|---|---|
| 5,049,462 | A | 9/1991 | Funhoff et al. |
| 5,237,392 | A | 8/1993 | Hickel et al. |
| 5,313,264 | A | 5/1994 | Ivarsson et al. |
| 5,485,277 | A | 1/1996 | Foster |
| 5,917,607 | A | 6/1999 | Naya |
| 6,441,906 | B2 | 8/2002 | Dickopf et al. |
| 6,493,097 | B1 | 12/2002 | Ivarsson |
| 6,686,582 | B1 | 2/2004 | Voelcker et al. |
| 6,714,303 | B2 | 3/2004 | Ivarsson |
| 6,999,175 | B2 | 2/2006 | Ivarsson |
| 2003/0048452 | A1 | 3/2003 | Johansen |
| 2004/0090630 | A1 | 5/2004 | Tittel et al. |
| 2007/0087348 | A1 | 4/2007 | Notcovich et al. |

FOREIGN PATENT DOCUMENTS

| | | |
|---|---|---|
| EP | 0469377 | 2/1992 |
| JP | 2002-214131 | 7/2002 |
| WO | WO 2006/107967 | 10/2006 |
| WO | WO 2010/122547 | 10/2010 |

OTHER PUBLICATIONS

International Preliminary Report on Patentability Dated Nov. 3, 2011 From the International Bureau of WIPO Re. Application No. PCT/IL2010/000306.

International Search Report and the Written Opinion Dated Sep. 30, 2010 From the International Searching Authority Re. Application No. PCT/IL2010/000306.

Notice of Allowance Dated May 8, 2013 From the US Patent and Trademark Office Re. U.S. Appl. No. 12/762,338.

Official Action Dated Nov. 2, 2012 From the US Patent and Trademark Office Re. U.S. Appl. No. 12/762,338.

Official Action Dated Mar. 12, 2012 From the US Patent and Trademark Office Re. U.S. Appl. No. 12/762,338.

Restriction Official Action Dated Dec. 21, 2011 From the US Patent and Trademark Office Re. U.S. Appl. No. 12/762,338.

Hickel et al. "Surface Plasmon Microscopy Characterization of External Surfaces", Journal of Applied Physics, 66(10): 4832-4836, Nov. 15, 1989. Abstract.

Hickel et al. "Surface Plasmon Optical Characterization of Lipid Monolayers A 5?m Lateral Resolution", Journal of Applied Physics, 67(8): 3572-3575, Apr. 15, 1990. Abstract.

Oda et al. "Instantaneous Observation of Angular Scan-Attenuated Total Reflection Spectra", Optics Communications, 59(5,6): 361-365, Oct. 1, 1986.

NON-SCANNING SPR SYSTEM

RELATED APPLICATION

This application is a continuation of U.S. patent application Ser. No. 12/762,338 filed on Apr. 18, 2010, which claims the benefit of priority under 35 USC 119(e) of U.S. Provisional Patent Application No. 61/170,679 filed Apr. 20, 2009. The contents of which are incorporated herein by reference in their entirety.

FIELD AND BACKGROUND OF THE INVENTION

The present invention, in some embodiments thereof, relates to a system for measuring reflectivity for multiple samples and angles of incidence, and more particularly, but not exclusively, to a surface plasmon resonance (SPR) system which allows simultaneous measurements of a two-dimensional array of samples.

In surface plasmon resonance, the intensity of light reflected from a thin metal surface (typically about 50 nm thick) decreases at a specific range of angles of the illumination relative to the metal surface. The illumination angle of greatest light absorption is sensitive to the refractive index of the material that is in direct contact with the other side of the metal layer. As shown in FIG. 1, the metal layer may be coated on the face of a prism, and the light passed through the prism to reflect from the back of the metal layer. FIG. 2 shows a typical reflectance as a function of angle of incidence, with a sharp dip at the SPR angle.

Typically, the front of the metal surface is exposed to a fluidic system that delivers the fluid containing samples or other materials automatically or manually. The fluidic system is usually made of one or more rubber or elastic polymer flow channels that are attached to the prism to generate a closed flow cell. This is shown in FIG. 3, where an elastic flow channel 300 is attached to a metal layer 106. The fluid flows from the left side and above the metal layer which can be coated with a ligand or capturing agents. The fluid itself can contain target molecules or analytes which are captured by the molecules or binding sites on the metal layer.

The addition of mass on the metal surface (as a consequence of binding for example) causes the SPR curve to shift on the angle axis, as shown in FIG. 4. This shift is measured as a function of time and displayed to the user as a measured signal. The shift can be interpreted as being proportional to the amount of molecules that are captured by the sensing surface.

By recording the shift of the SPR curve as a function of time, it is possible to measure the association and dissociation curves of molecules to other molecules. One possible method to extract reaction constants, rates and equilibrium is by fitting binding models to these curves. An example of this kind of curve is shown in FIG. 5.

U.S. Pat. No. 5,313,264, to Ivarsson, describes an optical biosensor system based on the evanescent wave phenomenon at total internal reflection, including SPR. The system reflects light over a range of angle of incidence from a set of sensing surfaces arranged in a row, horizontally. Using an anamorphic lens system, with different focal lengths in the horizontal and vertical planes, the reflected light is focused on a two-dimensional array of individual photodetectors, with different photodetectors in the same column representing different angles of incidence for the same sensing surface, and different photodetectors in the same row representing different sensing surfaces for the same angle of incidence.

Published European patent application EP0341928, to Finlan et al, describes an SPR system for detecting the distribution, in two dimensions, of DNA fragments undergoing electrophoresis on a sensing surface. A point or line of illuminating light is scanned over the surface. The illuminating light has a narrow range of angles of incidence that includes the SPR dip, and a photodetector, synchronized to the scan, measures the reflected light from each area on the surface, and detects a decrease in light reflected from those areas where a stronger SPR dip occurs.

SUMMARY OF THE INVENTION

An aspect of some embodiments of the invention concerns a system for measuring an evanescent wave phenomenon at total internal reflection, such as SPR, in which areas of interest are arranged over a surface are illuminated over a range of angles of incidence, an image of the surface is projected to a set of secondary focusing elements, and the secondary elements project the light reflected at each angle of incidence from each area of interest to different areas of a two-dimensional light detector.

There is thus provided, in accordance with an exemplary embodiment of the invention, a system for measuring an evanescent wave phenomenon at total internal reflection, the system comprising:
  a) a sensing surface comprising a plurality of areas of interest;
  b) an illumination sub-system comprising a light source, which illuminates each area of interest on the sensing surface over a range of angles of incidence;
  c) a detector which responds differently to an intensity of light received by it at different locations; and
  d) projection optics comprising primary optics and a plurality of secondary elements, the primary optics projecting an image of the illuminated sensing surface onto the secondary elements, which project their received light onto the detector in such a way that it is possible to determine, from the response of the detector, how much light is reflected from each area of interest, as a function of angle of incidence over the range of angles for that area.

Optionally, the evanescent wave phenomenon comprises surface plasma resonance (SPR), and the sensing surface comprises a material that exhibits SPR.

Optionally, the areas of interest are arranged in two dimensions on the sensing surface.

Optionally, the illumination sub-system is configured to illuminate all areas of interest simultaneously.

Optionally, for each area of interest, the illumination sub-system is configured to illuminate said area of interest over the entire range of angles of incidence simultaneously.

In an embodiment of the invention, the detector comprises a plurality of detector elements, and the different response of the detector to light received at different locations is due to a different response of the detector to light received by different detector elements.

Optionally, the detector responds substantially simultaneously to light received by different detector elements.

Optionally, the detector elements are arranged on the detector in a regular one-dimensional or two-dimensional array.

Optionally, the detector elements are arranged on a surface of the detector in two dimensions.

Optionally, the system is configured so that light reflected from each area of interest, at each angle of incidence in the range for that area, is received by the elements of the detector with a substantially different distribution of intensities, thereby making it possible to determine, from the response of the detector, how much light is reflected from each area of interest, as a function of angle of incidence.

Optionally, the projection optics projects light reflected from each area of interest, within each of a plurality of sub-ranges of angles of incidence for that area of interest, mostly to detector elements that receive more of the light reflected from that sub-range and that area of interest than from any other sub-range or area of interest.

Optionally, the detector elements comprise a plurality of detector regions arranged in two dimensions on a surface of the detector, each area of interest corresponding to one detector region, with the detector elements in each region receiving light mostly from the corresponding area of interest.

Optionally, within each detector region, at least some of the detector elements, that receive more of their light from one sub-range of angles of incidence, and from the area of interest corresponding to that detector region, than from any other sub-range or area of interest, are arranged on the surface of the detector such that an average angle of incidence in the sub-range that an element receives the most light from is a monotonic function of the position of the element along an axis.

In an embodiment of the invention, the system also includes one or more fluid channels capable of bringing one or more sample fluids in contact with at least some of the areas of interest, each such area comprising a surface suitable for the evanescent wave phenomenon that specifically binds at least one material from a sample fluid that is brought in contact with that area, if said material is present in said fluid.

Optionally, for at least a first and a second one of said areas of interest, the surface of the first area binds a different material than the surface of the second area.

Optionally, the one or more fluid channels comprise at least two fluid channels capable of bringing different sample fluids in contact with at least two different areas of interest, each such area comprising a surface suitable for the evanescent wave phenomenon that specifically binds to at least one material from a sample fluid that is brought in contact with that area, if said material is present in said fluid.

Optionally, at least one area of interest is a reference area that is not in contact with any of the fluid channels, or does not bind specifically to any material, or both.

Optionally, the system includes an analyzer which calculates a concentration of the material in the sample fluid, a reaction rate of the material with the surface, or both, using data of the response of the detector as a function of time.

Optionally, the range of angles of incidence for at least some of the areas of interest includes a peak absorption angle of incidence for said area of interest.

In an embodiment of the invention, the secondary elements comprise a plurality of lenslets.

Optionally, the lenslets are cylindrical.

Optionally, for each area of interest, there is at least one secondary element that projects to the detector substantially only light reflected from that area of interest.

Optionally, for at least one area of interest, the at least one secondary element comprises a plurality of secondary elements, each projecting light reflecting from that area of interest to the detector in a way that produces a different response of the detector.

Optionally, the system is configured so that substantially all of the light reflected from the sensing surface and reaching the detector was of a polarization subject to the evanescent wave phenomenon when it reflected from the sensing surface.

In an embodiment of the invention, the system also comprises:
a) inactive areas not exhibiting the evanescent wave phenomenon, located between at least two of the areas of interest, wherein the projection optics projects light reflecting from the inactive areas to the detector; and
b) an image analyzer that analyzes data from the detector, and uses software to distinguish data of light reflected from the areas of interest, from data of light reflected from the inactive areas.

Optionally, at least part of the illumination system is mounted so that it can be moved or tilted to adjust the ranges of angles of incidence for one or more areas of interest.

There is further provided, in accordance with an exemplary embodiment of the invention, a method of detecting materials in fluid samples using an evanescent wave phenomenon, the method comprising:
a) passing one or more fluid samples, containing at least one material, over a plurality of areas of interest, arranged on a sensing surface, which exhibit the evanescent wave phenomenon, and at least one of which binds to the material;
b) reflecting light from the plurality of areas of interest, over a range of angles of incidence for each area; and
c) projecting an image of the sensing surface to a plurality of secondary optical elements, with sufficiently sharp focus so that light reflected from different areas of interest is projected to substantially different secondary elements, and projecting the light from the secondary elements to a detector.

Optionally, the method also comprises determining, from a response of the detector, how much light is reflected from each area of interest, as a function of angle of incidence over the range of angles for that area, for at least one time interval.

Optionally, the method also comprises analyzing response data from the detector to determine one or more of a presence, a concentration, and a reaction rate of the material in the one or more samples.

Optionally, the evanescent wave phenomenon comprises SPR.

Optionally, reflecting light from the plurality of areas of interest comprises reflecting light simultaneously from the plurality of areas of interest.

Additionally or alternatively, reflecting light from the plurality of areas of interest comprises, for each area of interest, reflecting light simultaneously from the range of angles of incidence.

Optionally, for at least two of the areas of interest, the range of angles of incidence includes an angle of incidence of measurable absorption.

Optionally, passing one or more fluid samples comprises passing at least two fluid samples, each over a different one of the at least two areas of interest.

Optionally, passing one or more fluid samples comprises passing one or more fluid samples containing between them at least two different materials, each of the materials binding to a different one of the at least two areas of interest.

Optionally, passing one or more fluid samples comprises passing a fluid sample over at least one area of interest that does not bind to the material, and analyzing the response data of the detector comprises comparing the response data from light reflecting from the area that binds to the material, to the response data from light reflecting from the area that does not bind to the material.

In an embodiment of the invention, analyzing the response data comprises comparing the response data from light reflecting from the area of interest that binds to the material, to response data from light reflecting from an area that does not exhibit the evanescent wave phenomenon, or from an area for which the range of angles of incidence does not include the range of angles of incidence substantially exhibiting the evanescent wave phenomenon.

Optionally, analyzing the response data comprises combining response data from light reflecting from neighboring areas of interest.

Additionally or alternatively, analyzing the response data comprises combining response data from light projected onto the detector at neighboring locations.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to a system for measuring reflectivity for multiple samples and angles of incidence and more particularly, but not exclusively, to a surface plasmon resonance (SPR) system which allows simultaneous measurements of a two-dimensional array of samples. The methods and devices described herein are not limited to use with surface plasmon resonance, but it should be understood that they can also be used with related optical measurements using evanescent wave phenomena at total internal reflection, such as Brewster angle reflectometry, or critical angle reflectometry, even though, for ease of exposition, only SPR will generally be referred to in the description.

An aspect of some embodiments of the invention concerns a system for measuring an evanescent wave phenomenon at total internal reflection, comprising a plurality of areas of interest arranged on a sample surface, which are illuminated over a range of angles of incidence, for example a range of angles relevant for SPR, and imaged by primary optics which projects the images onto a plurality of secondary optical elements, for example one or more elements for each area of interest. The secondary elements, for example an array of lenses, project the light they receive onto a light detector, such that it is possible to measure the reflected light intensity as a function of angle of incidence for each of the areas of interest. Optionally, the areas of interest are arranged in two dimensions on the sample surface. Optionally, the different areas of interest are each illuminated over a range of different angles of interest simultaneously, and the reflected light is projected simultaneously to different areas of the light detector. For example, light from each area of interest may be projected to a different small area of the detector, and within each of these small areas, light from different angles of incidence may be spread out in one dimension by the secondary elements. Having the areas of interest arranged two-dimensionally on the sample surface, rather than only one-dimensionally, has the potential advantage that a much larger number of areas of interest can be analyzed simultaneously.

Optionally, fluid channels bring one or more sample fluids to different areas of interest, and optionally the areas of interest bind material in the sample fluids. Optionally, different areas of interest bind different materials in the sample fluids. Optionally, one or more of the areas of interest do not come in contact with a sample fluid, or only come in contact with water or an inert fluid, or do not bind any material, and are used for calibration, for example. Optionally, the secondary optical elements comprise cylindrical lenses. Optionally, the light detector comprises a two-dimensional array of detector elements (pixels). Optionally, each pixel receives light primarily from one area of interest and one range of angles of incidence.

Figure 1:
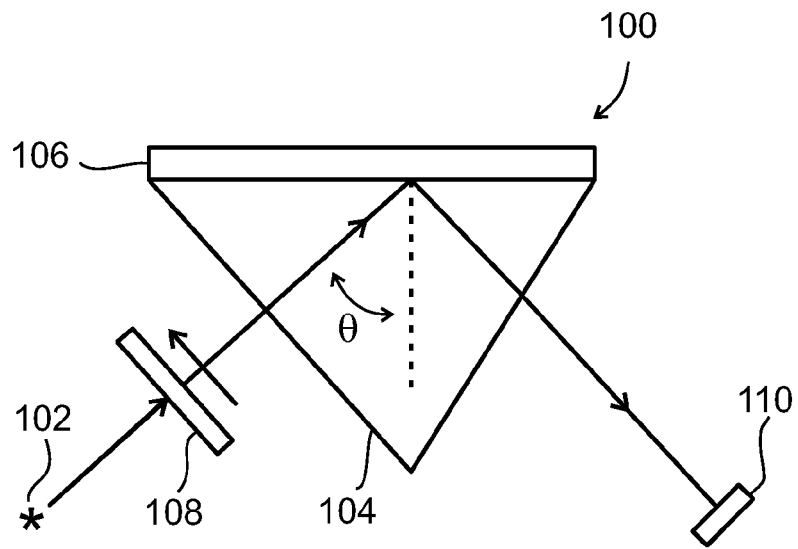
FIG. 1 is a schematic side view of an SPR system, according to the prior art.

For purposes of better understanding some embodiments of the present invention, as illustrated in FIGS. 1-5 of the drawings, reference is first made to the construction and operation of a conventional (i.e., prior art) SPR system 100, as illustrated in FIG. 1. A light source 102 transmits a light beam to illuminate a sensing surface on one of the facets of a dielectric prism 104. The surface of the prism is coated with a thin metal layer 106, for example Au, Ag, Al or any other metal that exhibits surface plasmon resonance. The light beam is polarized with a polarizer 108 in a 'P' state, with the electric field of the light wave having a component normal to the surface of the metal layer, to eliminate the 'S' state, with electric field parallel to the surface of the metal layer, that does not generate SPR waves in the metal layer. After the light reflects from the back of the metal layer at an angle of incidence θ and interacts with it, it passes through the other facet toward a detector 110. The detector could be any type of optical sensing device, for example a single detector, a one dimensional detector array, or a two dimensional detector array.

Figure 2:
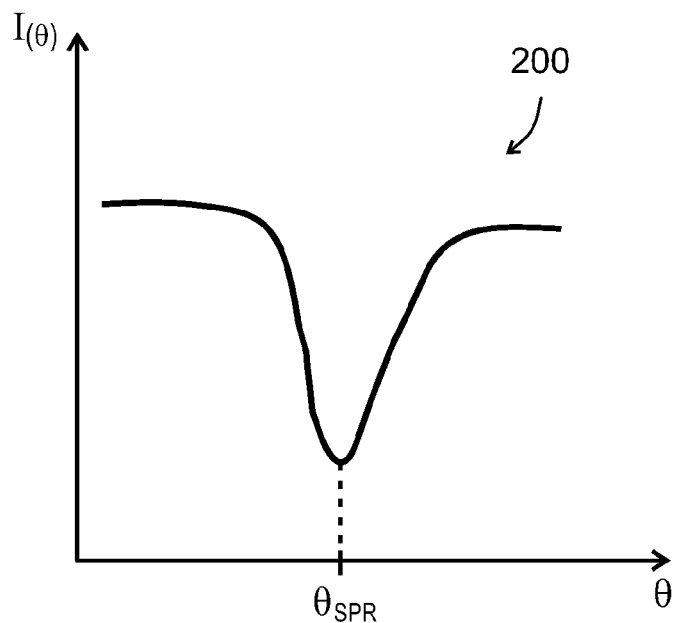
FIG. 2 is a schematic plot of reflected intensity as a function of angle of incidence for an SPR surface, according to the prior art.

FIG. 2 shows a plot 200 of a typical SPR curve, which is the reflected intensity I as a function of the angle of incidence θ. This curve depends on the illuminating wavelength, prism refractive index, metal layer refractive index and the material attached to the front surface of the metal layer, outside the prism.

Figure 3:
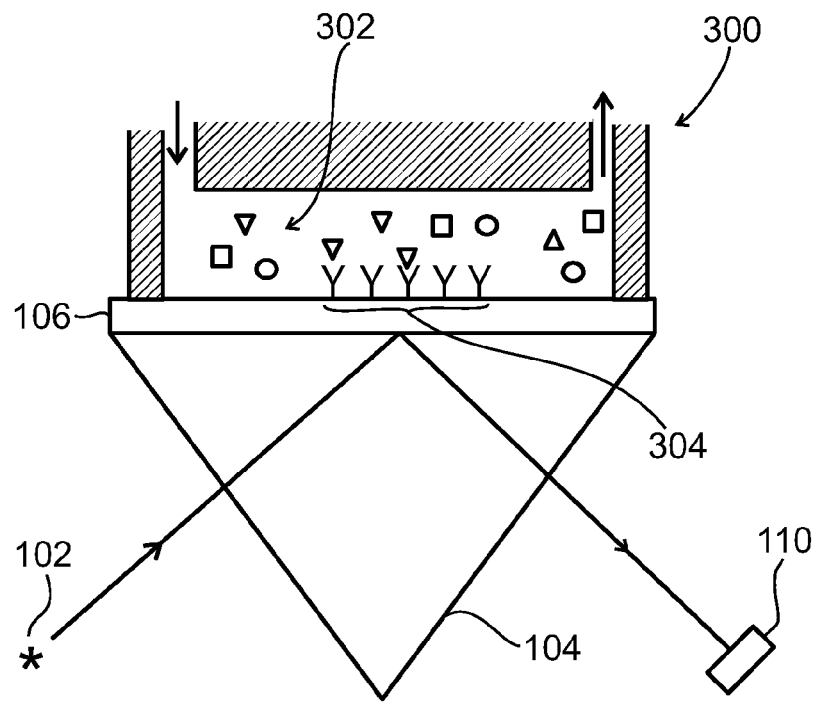
FIG. 3 is a schematic side view of a fluidic system for SPR, according to the prior art.

FIG. 3 schematically shows a cross-sectional view of a fluidic system 300 used with an SPR system such as system 100 shown in FIG. 1. Fluidics system 300 is attached to prism 104 in order to deliver samples 302 and other materials into contact with metal layer 106 where the sensing takes place. A ligand 304 adhering to a sensing area of metal layer 106 selectively binds to analyte molecules of interest, affecting the SPR curve of the metal layer.

Figure 4:
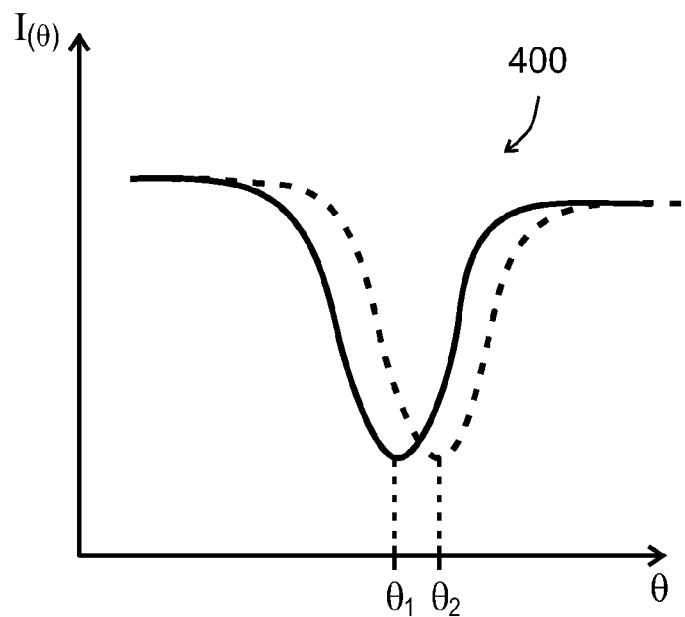
FIG. 4 is a schematic plot of reflected intensity as a function of angle of incidence for an SPR surface, showing the change due to attachment of molecules on the surface, according to the prior art.

FIG. 4 schematically shows a plot 400 of an SPR curve, illustrating a shift in the angle of minimum reflectivity, from $\theta_1$ to $\theta_2$, due to binding of molecules to the SPR sensing area. $I(\theta)$ is the measured light intensity at the detector as a function of the angle of incidence. Such a shift may also occur due to a change in the refractive index of the fluid that is in contact with the sensing area.

Figure 5:
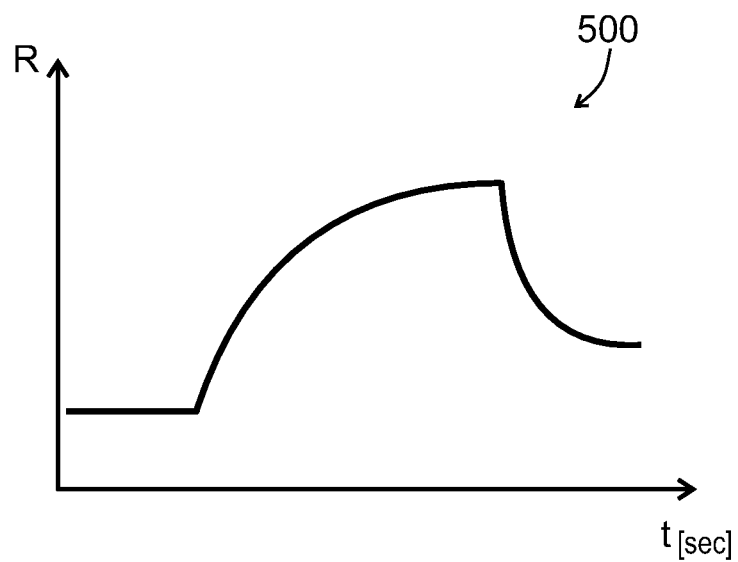
FIG. 5 is a schematic plot of SPR response as a function of time, according to the prior art.

FIG. 5 illustrates a plot 500 of an SPR response R as a function of time t. R is, for example, an angle of incidence at which the reflectivity is at a minimum. The rising curves may represent binding of molecules to the sensing area, while the falling part may represent dissociation of the molecules.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 6:
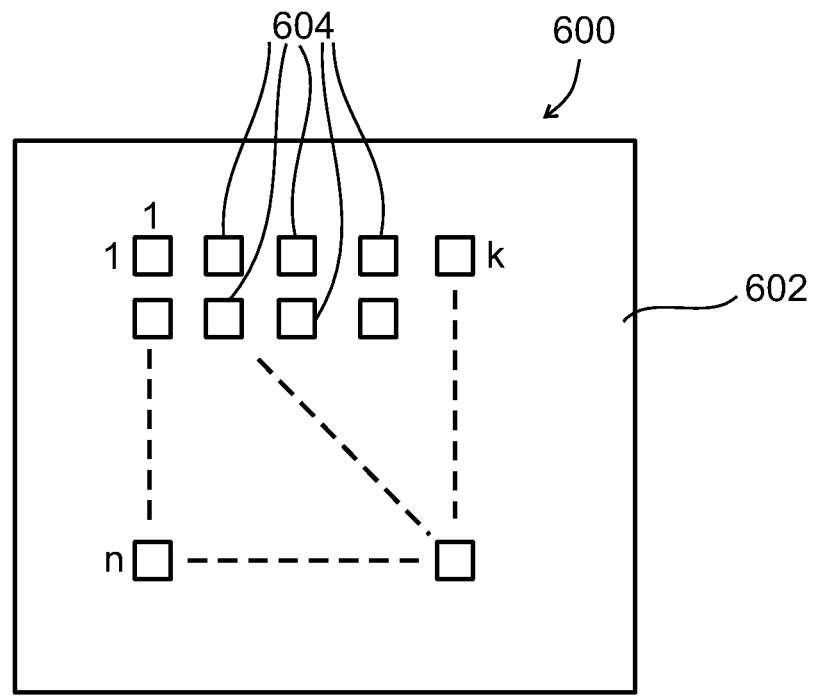
FIG. 6 schematically shows a two-dimensional array of areas of interest for SPR, according to an exemplary embodiment of the invention.

Referring now to the drawings, FIG. 6 illustrates an arrangement 600 of a plurality of measurement sites on a same prism in an SPR system, made by dividing a sensing surface 602 into a plurality of areas of interest 604. The areas of interest are optionally arranged two-dimensionally on the sensing surface, for example in a two dimensional array having n-by-k elements, with n and k both greater than 1.

In an exemplary embodiment of the invention, the light source is comprised in an illumination sub-system, optionally also including illumination optics, designed to illuminate the sensing surface with a range of angles of incidence, optionally illuminating with the whole range of angles simultaneously, and optionally illuminating all areas of interest of the sensing surface simultaneously. The range of angles optionally includes at least some angles that are included in the SPR dip as shown in FIG. 4, optionally the entire range of angles in the SPR dip for more precise measurement of the dip angle, and may also contain a wider range of angles in order to extend the dynamic range of the measurement. Although the illumination sub-system may illuminate the sensing surface at different angles of incidence sequentially, and/or may illuminate different areas of interest sequentially, simultaneous illumination of all areas of interest at all angles of incidence in the range has the potential advantages of allowing the measurements to be made more quickly, and possibly avoiding a need for moving parts in the illumination sub-system.

Optionally, the entire sensing surface, more than 90% or 80% or 50% of the sensing surface, is simultaneously illuminated substantially uniformly, for example with light intensity that varies by less than a factor of 2, or 1.5, or 1.2. Optionally, any non-uniformity in illumination intensity is predominantly on the scale of the entire sensing surface, rather than on the scale of the individual areas of interest. This has the potential advantage of allowing the illumination sub-system to be simpler than if, for example, different areas of interest were illuminated separately. Alternatively, the areas of interest are illuminated at substantially higher average intensity, for example higher by at least a factor of 1.5, or 2, or 5, than the average intensity of illumination for the portions of the sensing surface that are located between areas of interest. This has the potential advantage that it may reduce interference caused by light, reflected from the portions of the sensing surface that are located between areas of interest, reaching the detectors which measure reflected light from the areas of interest.

Optionally, as in FIG. 1, a polarizer between the light source and the sensing surface polarizes the light, so that much or substantially all of the light reaching the sensing surface is of a polarization subject to the evanescent wave phenomenon. Alternatively or additionally, the light source itself is polarized. Alternatively or additionally, a polarizer between the sensing surface and the detector polarizes the light so that most or substantially all of the light reaching the detector was of a polarization subject to the evanescent wave phenomenon, when it reflected from the sensing surface. In all of these cases, the system is configured so that most or substantially all of the light reflected from the sensing surface and reaching the detector was of a polarization subject to the evanescent wave phenomenon when it reflected from the sensing surface. A system with such a configuration may have the potential advantage, compared to a system using unpolarized light, that it has a higher signal to noise ratio, since more of the detected light is subject to the evanescent wave phenomenon that the system is measuring.

Figure 7:
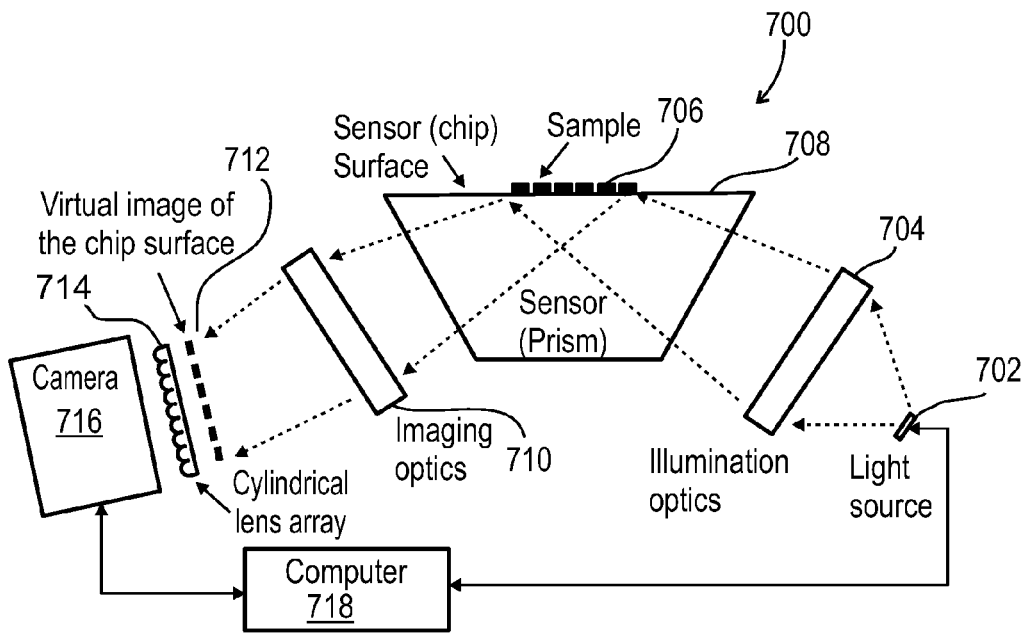
FIG. 7 is a schematic side view of an SPR system according to an exemplary embodiment of the invention.

FIG. 7 schematically shows an SPR system 700, according to an exemplary embodiment of the invention. As illustrated in FIG. 7, after illuminating light has interacted with a sample 706 on sensing surface 708, it is reflected or transmitted toward primary imaging optics 710, which project a real or virtual image 712 of the sensing surface on a set of secondary optical elements 714. The secondary elements optionally comprise, for example, an array of lenses, with light projected from different areas of interest on the sensing surface optionally projected to different lenses in the array. Each lens in the array, in turn, projects the light waves that arrive at it to a light detector 716 at different locations at its focal plane, depending on at least one component of their angle of propagation, and hence on their angle of incidence when reflecting from the sensing surface. Light waves projected by different lenses in the array also reach the light detector at different locations, making it possible to separately measure the intensity of reflected light from each area of interest at each angle of incidence. A controller 718, for example a computer, analyzes data from detector 716.

The illumination is provided by light source 702, which is, for example, a LED, laser diode, incandescent bulb, filament bulb, arc lamp, or any other light source known to the art. Particularly if the light source is intrinsically broadband, it is optionally provided with a band pass filter as part of illumination optics 704, to allow more precise measurement of the SPR curve, which depends on wavelength. The wavelength or wavelengths of the light source are optionally chosen to be in a range where the SPR phenomenon exists and optical components are available. Optionally, at least some of the different areas of interest are illuminated with different wavelengths or ranges of wavelength, for example to measure SPR as a function of wavelength, optionally for a same material and fluid sample. The light from the light source may be polarized by any kind of light polarizer, may be diffused by any kind of light diffuser, and may by filtered by any kind of wavelength filter, as part of illumination optics 704.

Primary imaging optics 710 may include any number of lenses and/or mirrors, including with positive or negative focal lengths, spherical or cylindrical surfaces, and other features of mirrors and lenses known in the art, as long as the primary optics projects an image of the sensing surface in reasonably good focus to the secondary optical elements 714. As will be described in more detail below, "reasonably good focus" means that the light waves reflected from different areas of interest of the sensing surface reach substantially different secondary elements, or different distributions of the secondary elements, enabling the light reflected from different areas of interest to be distinguished by the light detector 716. The secondary elements optionally comprise a cylindrical lens array (lenticular), or a spherical lens array.

The primary optics and secondary elements optionally also comprise polarizing and/or filtering components, for example in order to limit the detected light from a particular area of interest to a narrow range of wavelength, and/or to a particular polarization, which can make the SPR absorption curve sharper and easier to measure. Furthermore, such filters can pass different wavelength ranges for the light from different areas of interest, even if the light illuminating the different areas of interest all has a same broad range of wavelengths.

Detector 716 may be any kind of photosensitive device with two dimensional resolution, for example a two-dimensional array detector. Optionally, the detector comprises a single detecting element, or a one-dimensional array, or a reduced two-dimensional array, and achieves its full two dimensional resolution and range by scanning in time over different spatial locations receiving light reflected at different angles of incidence and/or from different areas of interest. It should be understood that "a detector which responds differently to an intensity of light received by it at different locations" as used herein may refer to a detector that responds differently to light received by a same detector element on a moving detector at different times during its scan, as well as to a detector that responds differently to light received by different detector elements of a stationary detector. However, using a detector with substantially simultaneous two-dimensional resolution, such as a two-dimensional array detector, has the potential advantage that the intensity of light reflected at different angles of incidence from different areas of interest can be measured substantially simultaneously, possibly allowing faster measurements, and possibly avoiding the need for moving parts. As used herein, "substantially simultaneous" detection or measurement of light means simultaneous within a time much shorter than the time over which the sample fluid flows past sensing surface 708, for example within a time shorter than 1 second, but would include, for example, serial as well as parallel transfer of data from the detector to a data processor.

Controller 718 may be connected to any of the above mentioned filtering and/or polarizing components in order to synchronize, control, move, manipulate, capture data, change intensity or perform any automated or manually controlled action on the system.

It should be noted, however, that a potential advantage of some embodiments of the invention is the ability to simultaneously measure complete SPR curves from multiple areas of interest, possibly all of a large number of areas of interest, without the need for any moving parts to scan over angle, or to scan over area of interest. For example, the sensing surface could comprise 10, 20, 30, 50, 100, 200, 300, or 500 areas of interest, or a greater or lesser or intermediate number, optionally arranged in a square or rectangular array. Optionally, measurements are made at 5, 10, 20, 30, 50 or 100 different angles of incidence, or a greater or lesser or intermediate number, optionally for each area of interest.

Figure 8:
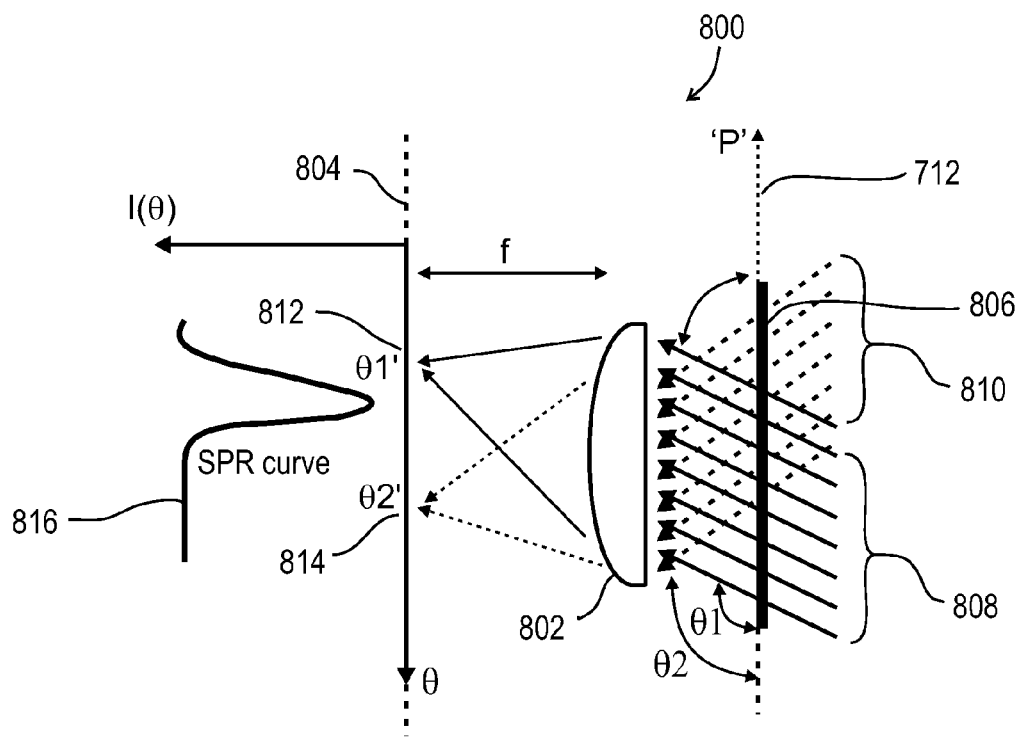
FIG. 8 is a schematic side view of a detail of secondary optical elements in an SPR system similar to that shown in FIG. 7, according to an exemplary embodiment of the invention.

FIG. 8 shows a more detailed view 800 of a cylindrical lens 802, one of the secondary optical elements 714, an array of cylindrical lenses, shown in of FIG. 7. FIG. 8 shows how cylindrical lens 802 transforms light from image plane 712, the plane of the projected image of the sensing surface, into intensity versus angle dependence on a detector plane 804. In this figure an area 806, shown in black, represents an image of an area of interest on SPR sensing surface 708 where an interaction takes place. The optical rays that arrive from primary imaging optics 710 (not shown in FIG. 8) from the right side converge at image plane 712, and form an image of the sensing surface. To the left of this image plane, the optical rays from a given point on the image start to diverge and get out of focus. However, the cylindrical lens is optionally close enough to the image plane so that substantially all of the light reaching this cylindrical lens comes from the same area of interest on the sensing surface, whether the cylindrical lens is directly at the image plane, or slightly behind it as shown in FIG. 8, or slightly in front of it. Here two families of rays are shown which approach the image plane with angles θ1 and θ2 (relative to image plane 712), corresponding to two different angles of incidence at the sensing surface. On detector plane 804 which is placed at the back focal plane of cylindrical lens 802, each family of rays that have the same angle relative to image plane 712 converges at the same point. For example, in FIG. 8, two families of parallel light rays are shown, light rays 808, shown as solid lines, with angle θ1, which converge at a point 812 on detector plane 804, and light rays 810, shown as dashed lines, with angle θ2, which converge at a point 814 on detector plane 804. If we consider the continuous case, where there are an infinite number of angles θ (in a finite range of angles), the intensity I as a function of vertical position on the detector plane is proportional to the intensity distribution as a function of the angle θ of the light rays as they approach the image of the sensing surface at imaging plane 712. If SPR sensing surface 708 has absorbance which depends on the angle of incidence of the illuminating light, then this dependence will be shown on the detector plane along the θ axis. This is shown schematically in FIG. 8 as a plot of curve 816 representing intensity I as a function of θ. Another way of looking at this scheme is by using plane wave decomposition of the image. It is well known that an image can be decomposed to a sum of plane waves, each one with its own amplitude and angle of incidence/exit. Each one of these plane waves converges at a different point along detector plane 804 with its own intensity. The cylindrical lens transforms the spatial distribution of light rays in the vertical direction from a distribution representing an image of the sensing surface at image plane 712, to a distribution representing the reflected light intensity vs. angle of incidence, at the detector plane 804.

It should be noted that since a cylindrical lens 802 is being used, the transformation to intensity versus angle of incidence takes place only in one dimension of the image. The dependence of the SPR absorbance on illumination angle is only in the 'P' direction of the illuminating light, the vertical direction in the plane of the drawing in FIGS. 7 and 8, and for this reason, this focusing of the light rays by the cylindrical lens is performed only in the plane of the drawing of FIG. 8. In the direction perpendicular to the plane of the drawing in FIGS. 7 and 8, the light rays are not focused by the cylindrical lens, in the system shown in FIG. 8, because in this direction (the 'S' direction), there is no dependence of the SPR absorption on the angle of incidence of the illuminating light. However, in some embodiments of the invention, one or more of the secondary optical elements are spherical lenses, or lenses of other shapes, or cylindrical lens with axis not quite perpendicular to the plane of the drawing, and some focusing does take place in the direction perpendicular to the plane of the drawing.

In some embodiments of the invention, light coming from different positions in the direction perpendicular to the plane of the drawing, from a given area of interest, has different wavelengths, either because the light illuminating that area of interest has different wavelengths across the area of interest in that direction, or because the reflected light is filtered to have different wavelengths in that direction. In this case, appropriately focusing the light in that direction can ensure that the different wavelengths are distinguishable because they reach different locations of the detector.

In FIGS. 7 and 8, image plane 712 of the sensing surface is close enough to the secondary optical elements, in this case an array of cylindrical lenses, so that substantially all of the light reaching each of the secondary elements comes from no more than one area of interest of the sensing surface. Optionally, the secondary elements project light from each area of interest to a different corresponding region of the detector, optionally with relatively little or no overlap of the different regions. Optionally, the detector comprises detector elements located in the different regions, with the different detector elements generating separately addressable data in response to the light they receive, and most or substantially all of the light received by a detector element in a given region comes from the corresponding area of interest. Optionally, within each region of the detector, at least some of the different detector elements mostly receive light reflected within different relatively small sub-ranges of angle of incidence, with different detector elements optionally together covering the whole range of angles of incidence for that area of interest. Optionally, for at least some of those detector elements, an average angle of incidence of the sub-range that the element mostly receives light from is a monotonic function of the position of the element along an axis, the vertical axis in the plane of the drawing in the case of FIG. 8. Such an arrangement has the potential advantage that it is easy to tell, when analyzing the detector data, how much light is reflected from each area of interest, as a function of angle of incidence.

In some embodiments of the invention, the image plane of the sensing surface may be further from the plane of the secondary optical elements, and/or the primary imaging optics may have poorer focusing properties, so that light reaching each secondary optical element comes substantially from two or more different areas of interest. Nevertheless, if the mix of contributions is sufficiently different for each secondary element, and if there are at least as many secondary elements as there are areas of interest, it may still be possible mathematically to separately find the contributions from each area of interest, for example by inverting a matrix.

It should be understood that, in some embodiments of the invention, the image plane and the detector plane referred to above may be curved surfaces rather than strictly planar surfaces, but they are still referred to herein as the image plane and the detector plane. Similarly, an array or set of detector elements, or of regions of a detector surface, is referred to herein as "two-dimensional" or "arranged in two dimensions" even if the elements or regions are arranged on a curved surface.

Figure 9:
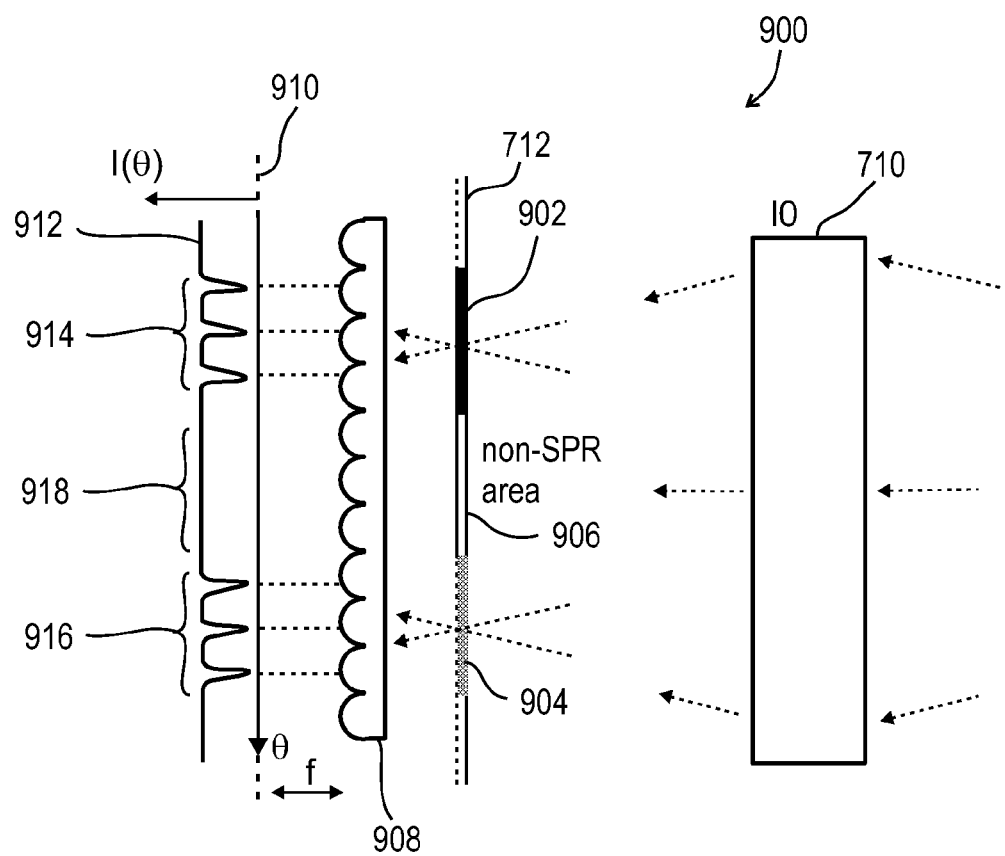
FIG. 9 is a schematic side view of a detail of secondary optical elements in an SPR system similar to that shown in FIG. 7, according to another exemplary embodiment of the invention.

In FIG. 9, a configuration 900 according to an embodiment of the current invention is shown. In FIG. 8, only one cylindrical lens was placed in front of the image of each area of interest, but in the general case, more than one lens can be placed in front of a single area of interest. This has some potential advantages, for example for eliminating any need for an adjustment mechanism that would adjust the location of the lens array to the locations of the images of the areas of interest in the image of the sensing surface. In some embodiments of the invention, however, such a mechanism is used.

In FIG. 9, light reflected from the sensing surface passes through primary imaging optics 710, which focuses the light to form an image of the sensing surface on plane 712. Light from a first area of interest is focused on an area 902, light from a second area of interest is focused on an area 904, and light from a part of the sensing surface between two areas of interest, where SPR does not occur, is focused on an area 906.

A secondary lens array 908 has three lenses adjacent to each of areas 902 and 904, and each of these three lenses, for each of areas 902 and 904, produces its own distribution of intensity as a function of position on a detector plane 910. The intensity I as a function of vertical position θ on detector plane 910 is shown schematically as a curve 912. In a region 914 where the light from area 902 is focused, there are three SPR dips in intensity, one for each lens in array 908 adjacent to area 902, and similarly there are three SPR dips in a region 916, one for each lens adjacent to area 904. In a region 918, which received light from area 906, there are no dips in intensity, because this light did not undergo SPR when it reflected from the sensing surface.

When there are a few lenses (secondary elements) per area of interest, it may be possible for software algorithms to find and recognize the regions of the light detector where there is data for SPR curves, such as regions 914 and 916, and to discard detector data for regions of the detector corresponding to unused areas of the sensing surface between areas of interest where there is no SPR data, such as region 918, or areas on the edges of the areas of interest, where it may not be possible to obtain good SPR curves. In a case of a single lens per area of interest it may be difficult to eliminate data from the edges of the areas of interest.

In the case of more than one lens per area of interest, the light intensity as a function of position on the light detector, in the plane of the drawing of FIG. 8 or 9, would repeat the SPR curve one or more times, for each area of interest. In this case, the analysis of an SPR shift, such as that shown in FIG. 4, can be carried out by various methods. One such method is to analyze the SPR shift for each repetition of the curve, and to average the final results for a specific area of interest. A second method is to average all the repetitions of the SPR curve for a specific area of interest, and then calculate the shift. In either case, data from repetitions of the SPR curve is optionally thrown out when the data seems bad, for example when it may come from the edge of the area of interest. Other methods are also possible.

The regions between the areas of interest are in some cases an inert material, for example a uniform rubber or elastomer that separates the areas of interest, and is attached to the sensing surface. In some cases, as in FIG. 3, such material may serve the purpose of separating the flow of different fluids over the sensing surface. If the refractive index of the rubber or Elastomer is large enough to be excluded from the dynamic range of angles of incidence of the measurement system, then the reflection from these areas has little or no dependence on the angle of incidence. This creates a flat, uniform measured intensity dependence on angle of incidence, for the relevant areas over the detector, as shown in region 918 in FIG. 9. By recognizing these uniform intensity areas, it may be possible to recognize with software the locations of the different areas of interest and the areas separating them.

Figure 10:
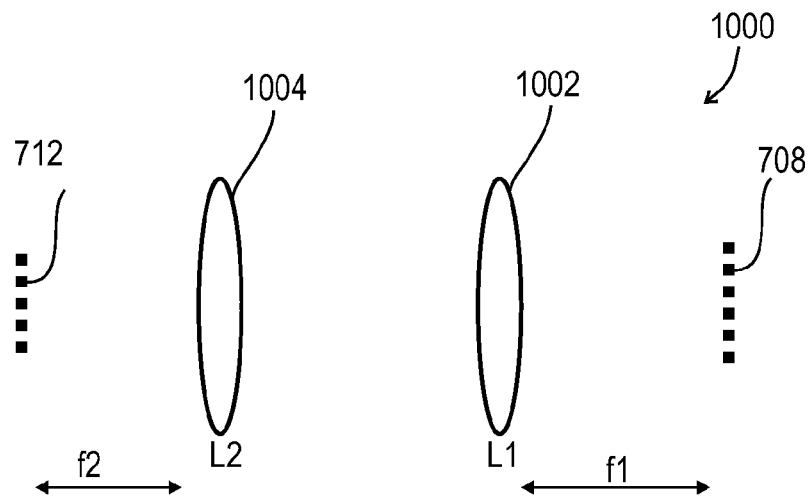
FIG. 10 is a schematic side view of imaging optics of an SPR system similar to that shown in FIG. 7, according to an exemplary embodiment of the invention.

FIG. 10 shows a configuration 1000 according to one possible embodiment of the primary imaging optics. It is composed of two lenses 1002 and 1004 of positive focal length, where a sensing surface 708 is located at one focal length from the first lens 1002, and an image of the sensing surface is located at a back focal plane 712 of lens 1004. It is possible to image the sensing surface by many other imaging systems, such as a single positive lens, or any other combination of optical components such as positive and negative lenses, concave and convex mirrors, aspheric optical components and all other means to produce an image at the desired plane.

Figure 11:
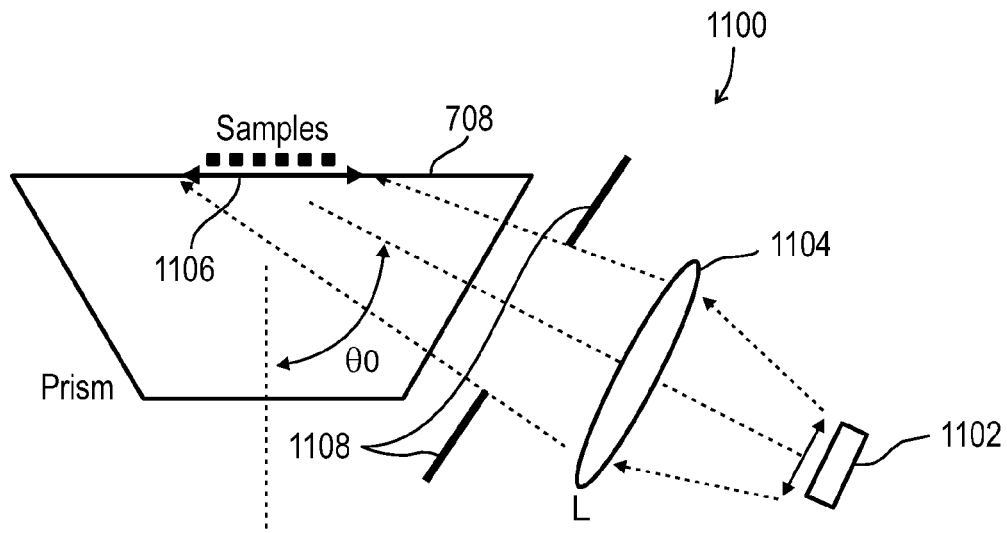
FIG. 11 is a schematic side view of illumination optics of an SPR system similar to that shown in FIG. 7, according to an exemplary embodiment of the invention.

FIG. 11 shows an illumination sub-system 1100 according to one possible embodiment of the invention. It may comprise a light source 1102 with a finite size, and illumination projection optics, such as a lens 1104, that projects an image 1106 of the light source on a sensing surface 708, where the biochemical interactions take place. In this type of illumination every point on the sample is illuminated with a range of angles that is determined by the magnification of the illumination projection optics, the source size, and the location and size of an optional angle stop 1108.

At least some areas of interest on the sensing surface are illuminated with a range of angles of incidence that includes at least part of the dip in the SPR absorbance curve. (Optionally, there may also be areas of interest, used for calibration for example, where the range of angles of incidence does not include any of the dip in the absorbance curve.) For these areas of interest, the range of angles of incidence that illuminates each point on the sample is determined by the above mentioned parameters of the illumination sub-system in a way that the range of angles can be used for measuring the SPR curve. A bias angle θ0 optionally determines an offset angle for the range of angles. This bias angle optionally causes the range of illumination angles to illuminate the sample at the angles close to or around the SPR absorbance angles.

It is important to note that there are many other options for illuminating the sample with a desired range of angles of incidence. For example, a source of finite size may be placed at a focal distance from the illumination lens, to illuminate the sample with a range of angles. Different combinations of distances between the light source and the illumination lens, and between the illumination lens and the sensing surface, are possible in order to change the distribution of angles of incidence of the light at the sensing surface. With some choices of parameters of the illumination sub-system, the range of angles of incidence may be different at different areas of interest.

It is also possible to use other optical components, such as additional lenses, reflectors, diffusers, polarizers, gratings and any means to illuminate the sample with a desired range of angles.

The illumination sub-system or part of it, in some embodiments of the invention, is mounted so it can be moved or tilted mechanically by means of motors or manually. This is optionally done to adjust or change the ranges of angles of incidence for the areas of interest, for example to adjust or change the offset angle θ0 in order to follow the location of the SPR curves.

Because the sensing surface is typically tilted at an oblique angle relative to the optical axis of the illumination projection optics, the illumination might not be evenly distributed over the sensing surface. In order to correct such non-uniformity in the intensity distribution, it is possible to tilt the source at an angle that will compensate for this problem. One possible angle for this tilt is a Scheimpflug angle according to the Scheimpflug principle. Other angles are also possible. Another method to overcome this problem is to place a gradient neutral density filter that compensates for the intensity gradients, with an inverse gradient of light absorption.

The image that is seen by the two dimensional detector is optionally composed of a plurality of substantially non-overlapping regions, one region corresponding to each area of interest. Optionally, the regions are arranged in two dimensions on a surface of the detector, if the corresponding areas of interest are arranged in two dimensions on the sensing surface. Each region has one or more stripes, each with a dark central fringe surrounded by lighter fringes. Each stripe is produced by one of the secondary optical elements, for example one of the cylindrical lenses in FIGS. 7, 8 and 9. The stripe or stripes in each region typically provide data about the SPR curve, a function of angle of incidence, for the corresponding area of interest. The angle of incidence at which the SPR curve has its greatest dip, for each area of interest, corresponding to the position of the dark central fringe within each stripe, is related to the amount of material captured by the sensing surface at that area of interest, or to a change in the refractive index of the material close to the sensing surface.

Figure 12:
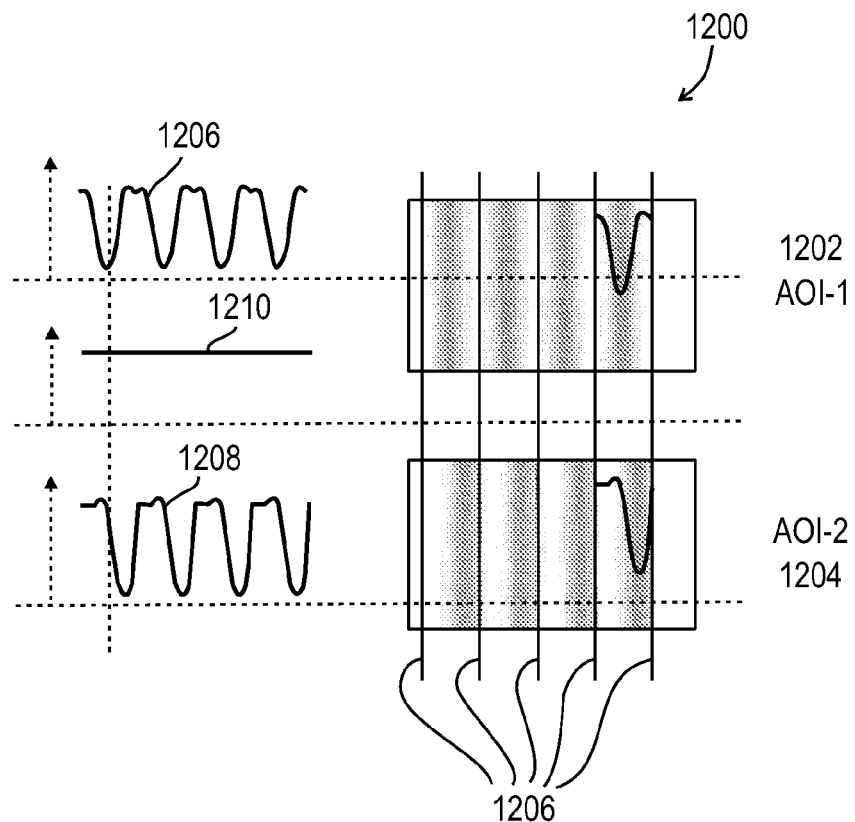
FIG. 12 is a schematic plot of light intensity as a function of position on a light detector, corresponding to two different areas of interest, using an SPR system similar to that shown in FIG. 9, according to an exemplary embodiment of the invention.

This is illustrated in FIG. 12, where a simulated captured image 1200 is shown for a zone of two areas of interest, corresponding to images 1202 and 1204, and for a separation area between them where there is no SPR. Image 1204 shows the intensity distribution for four cylindrical lenses with the dips in the SPR curves located at the right side of each of fiducial stripes 1206. When the refractive index is changed, the dips in the SPR curves shift to the left, as shown for image 1202. The intensity as a function of position in the image is shown in curve 1206 for image 1202, and in curve 1208 for image 1204. In between the two areas of interest there is an area where there is no SPR effect, because of a partition with a high refractive index material for example, where the light intensity is uniform. The intensity as a function of position in the image corresponding to this area is shown in curve 1210, a flat line.

Interpreting the captured images for a signal that shows the change in amount of adsorbed material on the sensing surface can be carried out by any of various methods. One can fit a theoretical or empirical function to the curves and find the shift in the dip as a free parameter, or as a function of a free parameter that can be found. This shift will be proportional to the change in refractive index (or amount of mass adsorbed on the chip surface). Other dependences which are not proportional are also possible. It is possible to find the shift in the dip by means of Fourier analysis and convolution theory, or by calculating the center of mass of the dip.

In order to improve signal to noise ratio (SNR), for each area of interest one can average all pixels in the perpendicular direction to the profile of the SPR curve (the direction perpendicular to the plane of the drawing in FIG. 7, 8, or 9) and therefore get a single SPR curve that is an average of all the curves along this direction and with a higher SNR. Averaging curves in time is also possible to increase SNR.

The number of secondary optical elements (such as cylindrical lenses) that can usefully be used per area of interest can vary from 1 up to half the number of pixels in the light detector along that direction, per area of interest. An optimal number can optionally be chosen from SNR considerations.

Areas between areas of interest that are not under the partition material can serve as reference areas. Blocked areas of interest, with no sample fluid flowing past them, or with an inert sample fluid such as distilled water, can also serve as reference areas of interest.

Figure 13:
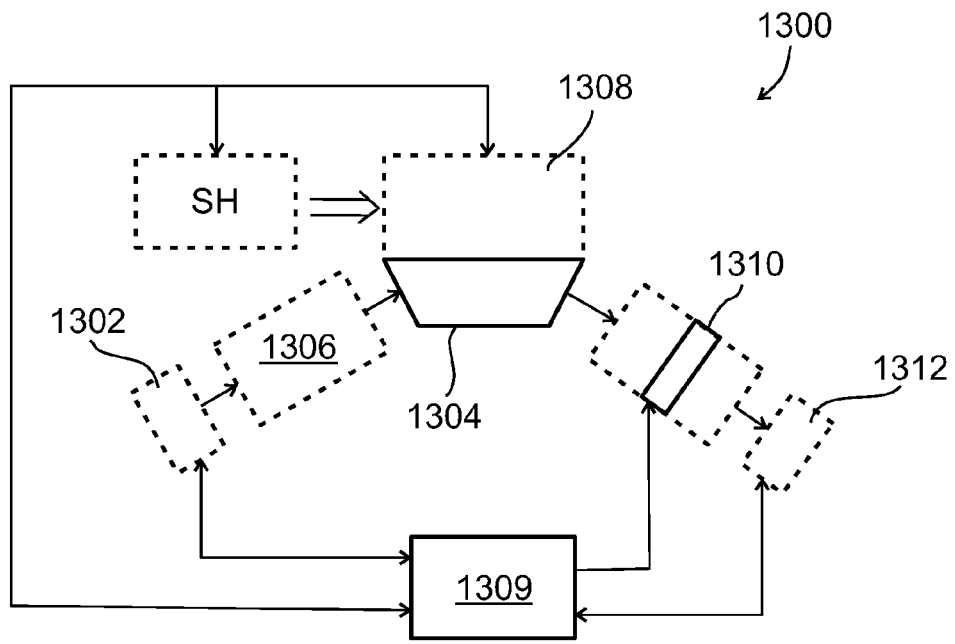
FIG. 13 is a block diagram for an SPR system similar to that shown in FIG. 7, according to an exemplary embodiment of the invention.

FIG. 13 schematically shows an example of an instrument 1300 that measures biochemical interactions and analyte concentrations, that is based on a SPR device. In general, such an instrument may comprise the following components, but is not limited to only those and does not have to contain all of them:

A light source 1302 transmits light waves towards a bio-chip sensor area 1304 which may be composed of a dielectric prism coated with one or more metals that enable SPR phenomenon, and may also include some dielectric layers for adhesion or SPR curve improvement. The light source may be a single element that transmits light waves, or a combination of many light sources. Light sources may be LED, diode lasers, incandescent bulbs, arc lamps, discharge lamps, lasers and many other electromagnetic wave emitting devices. The light source need not emit visible light, but, as used herein, "light" and "light source" may refer to infrared light, ultraviolet light, or electromagnetic radiation of any frequency that may be used for SPR or other optical reflectometry sensing methods. In order to improve measurement results, it is possible to stabilize the temperature of the light source by means of passive (isolation, thermal mass) or active (closed loop temperature controlled zone) mechanisms. This reduces intensity changes of the transmitted light, and wavelength changes.

Light from the light source optionally passes through illumination optics 1306 for illuminating the sensor area. The illumination optics may contain one or more lenses, mirrors, optical stops, prisms, electro-optical devices, apertures, polarizers, optical filters (neutral or wavelength dependent), phase masks, diffusers, gratings and any other optical devices that may be used to shape the light for improved performance of the SPR measurement. In some embodiments of the invention, some of the light is reflected out of the main optical path in order to sample it for referencing, normalizing and stabilizing the amount of light that is transmitted from the light source.

The bio-chip sensing surface is attached to a fluidic system 1308 that may deliver liquids or gases to the bio-chip sensing surface, where the SPR layer is used for measuring changes in the amount of adsorbed molecules or materials. The fluidic system may comprise one or more of tubings, all sorts of valves, check valves, all sorts of pumps, degassers and other elements that are used to deliver the samples and other liquids to a measurement zone comprising areas of interest on the sensing surface. The fluidics that is attached to the bio-chip sensing surface directly may be composed of a flexible material such as PDMS, silicon RTV or other type of polymer, elastomer or rubber in order to produce flowing zones or channels or small chambers over the bio-chip sensing surface by sealing these structures against the surface. Optionally, the fluidics comprises the "CrissCross" fluidics system described in US published patent application 2007/0087348 to Notkovich et al, which may be used to simultaneously measure binding reactions between each of a plurality of probes and a plurality of targets, using areas of interest arranged in a rectangular array on a sensing surface.

The fluidic system may be manually operated, or automated and controlled by a controller such as a computer 1309, or a combination of the two. Computer 1309, or another computer or controller, may also control light source 1302.

The measurement zone may be temperature controlled and/or stabilized in order to improve signal stability and perform experiments at different temperatures. The samples may also be held at different temperatures by controlling the temperatures of their reservoirs.

The light reflected from the bio-chip sensing surface then goes through collecting optics 1310 which directs this light toward one or more light detectors 1312, for imaging as well as for other purposes. The detectors may comprise a single detector such as a silicon photodiode, photomultiplier, avalanche photodiode or any other type of detector that can quantify the intensity of the delivered electromagnetic radiation. The detectors may also comprise a linear array of detector elements such as a line scan camera, or a combination of line scan detectors, and/or a two dimensional detector such as a CCD camera or a CMOS camera or any other type of array detector that is available. Combinations of different types of light detectors may be used in order to improve measurement performance. For example a two dimensional array detector may be used for the imaging, and a single detector for intensity control and referencing.

In an exemplary embodiment of the invention, collecting optics 1310 comprises imaging optics that images the biochip sensing surface, as described above for FIG. 7. The collecting optics may comprise any of the following components and devices: one or more lenses, mirrors, optical stops, prisms, electro-optical devices, apertures, polarizers, optical filters (neutral or wavelength dependent), phase masks, controllable stops (mechanical or electro-optical), lens arrays (such as cylindrical or spherical), lenticular arrays, gratings and many other optical devices that may be used to deliver the light to the detector. Computer 1309, or another computer or controller, optionally controls imaging optics 1310 and/or detector 1312, and/or receives and/or analyzes data from detector 1312.

Figure 14:
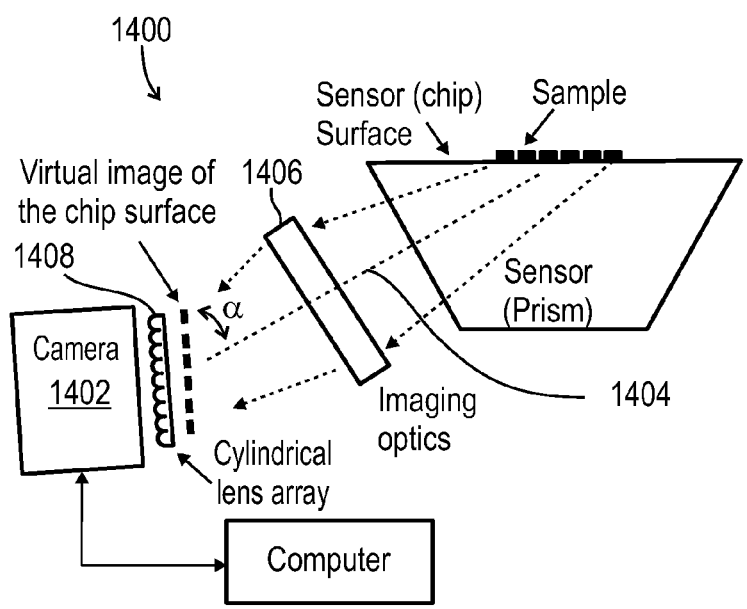
FIG. 14 is a schematic side view of the imaging portion of an SPR system similar to that shown in FIG. 7, according to an exemplary embodiment of the invention.

One possible embodiment of the imaging optics, as shown in FIG. 14, uses a Scheimpflug construction 1400, where an imaging detector 1402 is tilted with an angle α relative to an optical axis 1404. When using an array detector the detector may be tilted at an angle α to the optical axis because the sensing surface is imaged from an angle which is far from being perpendicular to the sensing surface. The tilt angle α is optionally determined by using the Scheimpflug construction rules. It is also possible to tilt the imaging lenses in a primary imaging optics 1406. A combination of the two is also possible in order to improve the imaging quality. A secondary lens array 1408 may also be tilted at an angle that is equal to α or another angle that will give improved performance of measuring the SPR curves. It is also possible to use an anamorphic lens system, and cylindrical lenses are shown in FIG. 14 as an example.

In a typical measurement process using light detectors, there may be some preceding calibration steps such as measuring and recording the response of the detector when the light source is turned off, for the purpose of dark subtraction. Another step may be to record the reflectance of the sensing surface while it is dry or covered with a fluid having a large refractive index (which shifts the SPR curve out of the dynamic range of the instrument) for the purpose of normalizing the signal that is collected later on, or for flat fielding.

Another possible procedure is to record the SPR curve that is measured when a neutral fluid such as distilled water or buffer is flowing over the sensing surface, and measuring the signal from an actual sample relative to this reference curve.

In some cases, the sensing surface includes reference spots, so that a reference signal can be used for calibration, in order to eliminate parasitic effects such as bulk effects, temperature variations, non-specific binding and other effects. The reference spots may be visible to the user as a standard area of interest in the array such as shown in FIG. 6, or they can be hidden in-between areas of interest in order to keep the user with as many available areas of interest as possible. Optionally, the measured signal is calibrated by simply subtracting the reference signal. More complicated adjustments to the signals are also possible for improving calibration, such as subtracting from a signal from one area of interest an average of signals from two or more nearby areas of interest. More complicated options are also possible, such as using weighted linear and nonlinear combinations of a neighborhood of the area of interest that is under investigation.

Secondary optical elements 1408, in the form of a cylindrical lens array for example, may be made of any dielectric material that can be shaped to form such an array, such as polymers, plastics, transparent rubbers and glass. The focal distance of the lenses in the array is determined by the radius of curvature of the lenses and the refractive index of the material that the array is made of. The secondary optical elements may also use diffractive and/or holographic effects.

Figure 15:
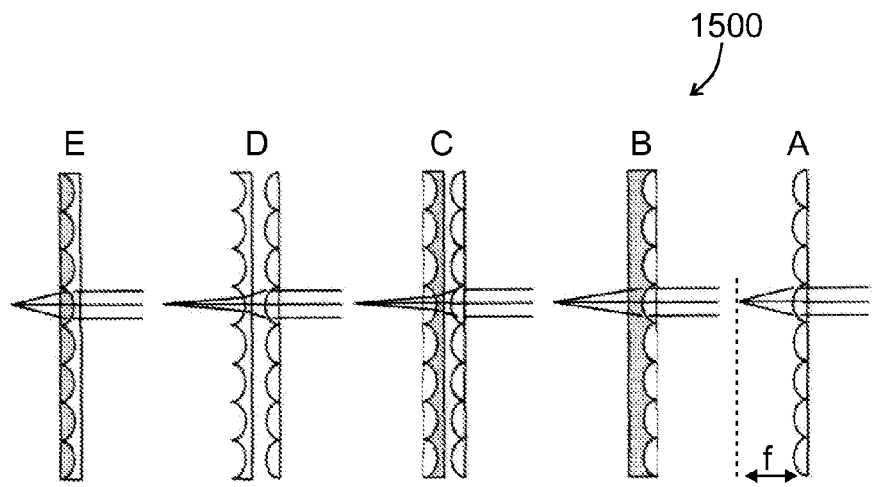
FIG. 15 is a schematic side view of secondary optical elements for an SPR system similar to that shown in FIG. 7, according to an exemplary embodiment of the invention.

FIG. 15 shows some possible embodiments 1500 of a cylindrical lens array with different focal lengths. The focal length affects the dynamic range and sensitivity of the system. Typically, the larger the focal length is, the smaller the dynamic range is, and the higher SNR is. This can be because with a large focal length, the angle resolution will be higher, but the range of angles of incidence that can be explored will be smaller. Cylindrical lens arrays are generally manufactured commercially with a predefined focal length, but there are several options for adjusting the focal length of an entire array or part of it.

In FIG. 15, a simple cylindrical lens array A is shown, with a focal length f. A cylindrical positive lens array B made of a dielectric material with refractive index n1 is also shown. On the convex side of array B there is a dielectric material of refractive index n2, which is lower than n1. This increases the focal length of the lens array, and the focal length can be tuned by controlling the refractive index n2. This material can be a fluid such as glycerol diluted with water, where the ratio of dilution determines the refractive index, and therefore the focal length. It can also be an optical adhesive material such as an epoxy, where the type of epoxy determines its refractive index. Any other material, with a well-defined index of refraction, that can be attached directly to the lens array can also be used here.

FIG. 15 also shows a combination C of a simple positive lens array attached to a cylindrical lens array which is coated with a material with refractive index n2 that is higher than the refractive index of the lens array n1. This causes the coated lens array to act as a negative lens array and therefore the combined focal lens of the simple positive lens array and the coated negative lens array is longer than the focal length of the simple lens array by itself. FIG. 15 also shows a combination D of a simple positive lens array combined with a simple negative lens array to increase the total focal length.

FIG. 15 also shows a simple negative lens array E coated with a material with refractive index n2 that is higher than the refractive index of the lens array n1. The coating is shown in grey. In this case the concave lens array becomes a positive lens array where the focal lens depends on the refractive index of the coating n2, as well as on n1. Higher n2 results in shorter focal length.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Figure 16:
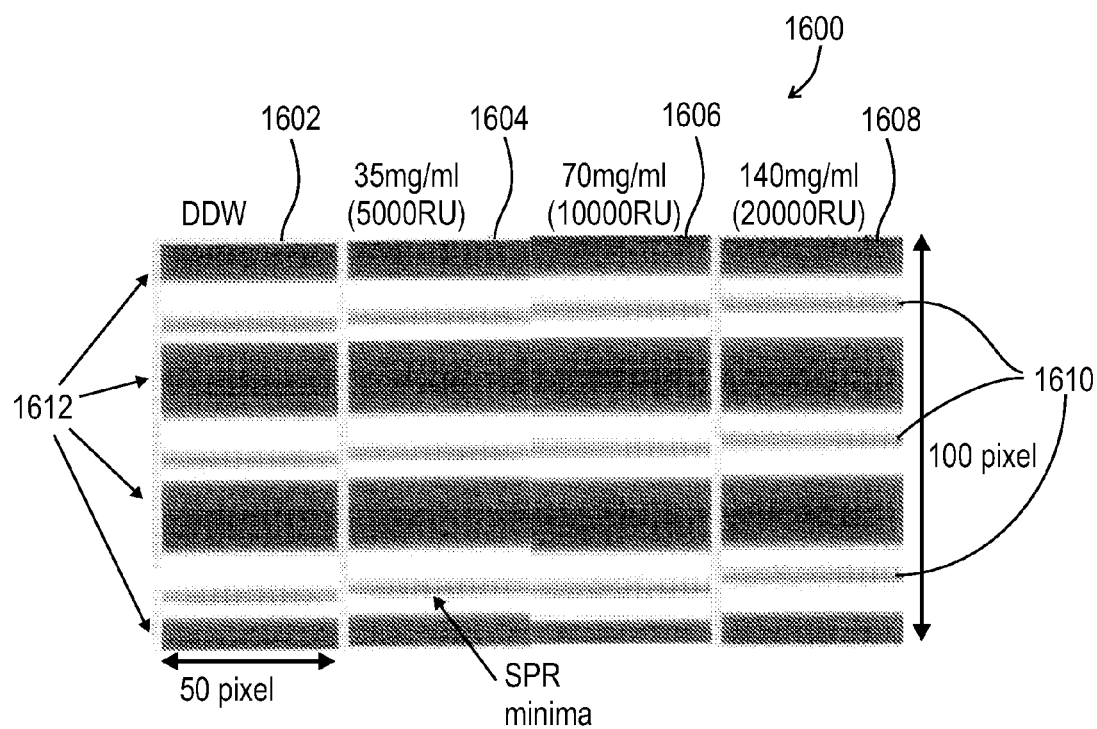
FIG. 16 is a plot of test data acquired with an SPR system, schematically illustrating what the light intensity as a function of position on a light detector might look like for the embodiment of the invention shown in FIG. 9.

FIG. 16 shows four images 1600, each of 50 by 100 pixels, that were captured by a CMOS camera, using an SPR system similar to that shown in FIG. 7, each image based on an SPR area of interest exposed to a different concentration of glucose solution as the sample fluid. The left most picture, image 1602, is for DDW (doubly distilled water, with zero concentration of glucose), the next one, image 1604, is for a solution of 35 mg of glucose in 1 ml of DDW, image 1606 is for a solution of 70 mg per ml, and image 1608 is for a solution of 140 mg per ml. Under each concentration, the relevant response in RU is given, where 1 RU=$10^{-6}$ change in refractive index of the sample fluid). One can see the shift of the SPR minima (the darker stripes 1610, each between two bright stripes) upwards, which means that the concentration of the solution in contact with the area of interest has increased. The thick dark stripes 1612 between the SPR curves are "dead" areas, where no light arrives at all because of the size and focal length of the cylindrical lens, since due to the configuration of the cylindrical lenses and the images of the areas of interest, all pixels were not being used.

In the case shown here, there are three SPR curves for this area of interest. During measurements, it is possible to calculate the SPR shift for each of the three separately, and then average, or alternatively, it is possible to average the curves to yield a single curve and then calculate the shift. Other methods and combinations are also possible. One can also calculate separately each curve and extract information on the uniformity of the area of interest.

Figure 17:
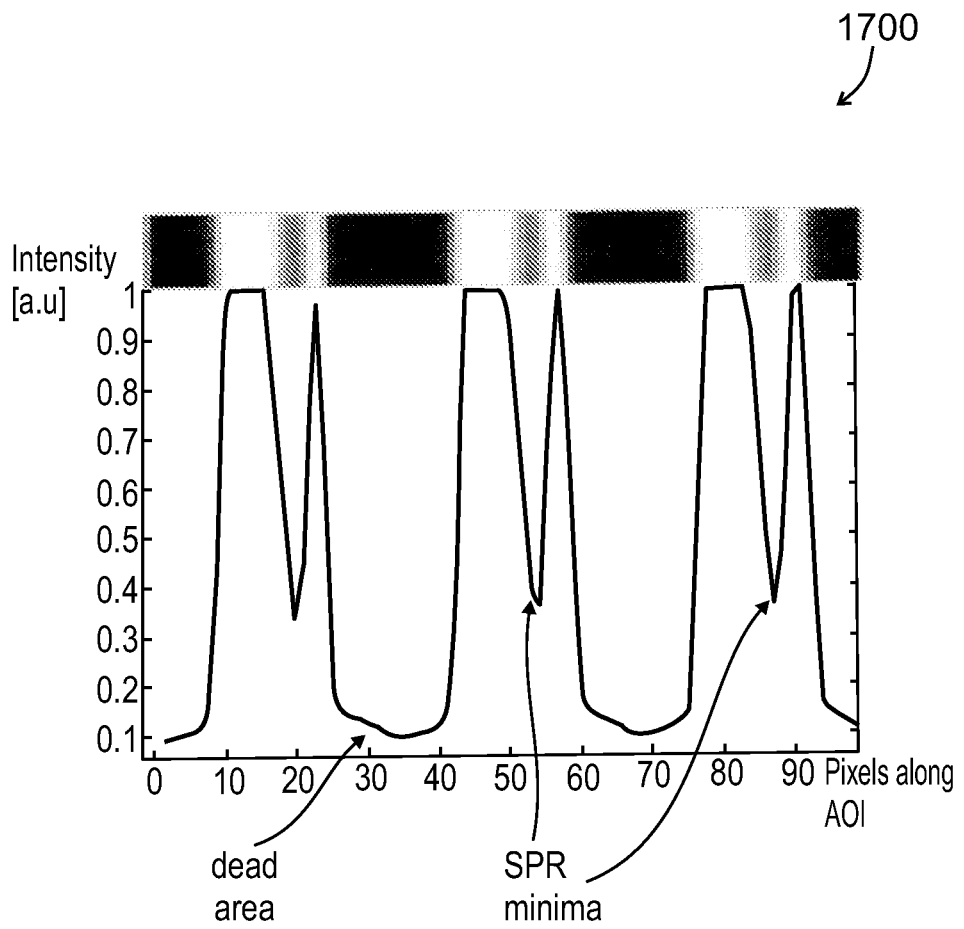
FIG. 17 is a schematic plot of the light intensity as a function of one coordinate, representing angle of incidence, for some of the test data shown in FIG. 16.

FIG. 17 shows an intensity profile 1700 across the area of interest that was shown on FIG. 16. Since there are 3 cylindrical lenses across the image of this area of interest, the cross section shows three SPR intensity curves. The intensity is optionally normalized by the saturation level of the CMOS camera, giving a value of 1 at pixels that were in saturation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for making measurements using an evanescent wave phenomenon at total internal reflection, the system comprising:
   a) a surface exhibiting the evanescent wave phenomenon at total internal reflection, comprising a plurality of sensing areas of interest, one or more of which are capable of binding to material in a fluid sample that comes in contact with them;
   b) an illumination sub-system comprising a light source, which illuminates each sensing area of interest on the sample surface over a range of angles of incidence;
   c) a detector which responds to an intensity of light received by it, the response being distinguishable for light received by the detector at different locations;
   d) primary optics that projects a real or virtual focused image of the illuminated sample surface; and
   e) a plurality of secondary elements, which receive light of the image projected by the primary optics and project their received light onto the detector, spreading out light reflected from each sensing area of interest at different angles of incidence to different locations on the detector;
   wherein the secondary elements are close enough to the focused image of the sample surface, and the detector is close enough to a focal plane of the secondary elements, so that it is possible to determine, from the response of the detector, how much light is reflected from each sensing area of interest, as a function of angle of incidence over the range of angles for that area; and
   wherein the sensing areas of interest are arranged one-dimensionally on the sample surface.

2. A system according to claim 1, wherein the detector comprises a plurality of detector elements, arranged in a one-dimensional array, and the response of the detector to light received at different locations is distinguishable due to different detector elements generating separately addressable data in response to the light they receive.

3. A system according to claim 1, wherein the evanescent wave phenomenon comprises surface plasmon resonance (SPR), and the sample surface comprises a material that exhibits SPR.

4. A system according to claim 1, wherein the illumination sub-system is configured to illuminate all sensing areas of interest simultaneously.

5. A system according to claim 1, wherein, for each sensing area of interest, the illumination sub-system is configured to illuminate said sensing area of interest over the entire range of angles of incidence simultaneously.

6. A system according to claim 1, wherein the detector comprises a plurality of detector elements, and the response of the detector to light received at different locations is distinguishable due to different detector elements generating separately addressable data in response to the light they receive.

7. A system according to claim 6, wherein the primacy optics and secondary elements project light reflected from each sensing area of interest, within each of a plurality of sub-ranges of angles of incidence for that sensing area of interest, mostly to detector elements that receive more light reflected from that sub-range and that sensing area of interest than from any other sub-range or sensing area of interest.

8. A system according to claim 1, also including one or more fluid channels capable of bringing one or more sample fluids in contact with at least some of the sensing areas of interest, each such area comprising a surface suitable for the evanescent wave phenomenon that specifically binds at least one material from a sample fluid that is brought in contact with that area, if said material is present in said fluid.

9. A system according to claim 8, including an analyzer which calculates one or more of a concentration of the material in the sample fluid, a binding rate of the material to the surface, and a dissociation rate of the material from the surface, using data of the response of the detector as a function of time.

10. A system according to claim 1, wherein the secondary elements comprise a plurality of lenslets.

11. A system according to claim 10, wherein the lenslets are cylindrical.

12. A system according to claim 1, wherein for each sensing area of interest, there is at least one secondary element that projects to the detector substantially only light reflected from that sensing area of interest.

13. A system according to claim 12, wherein, for at least one sensing area of interest, the at least one secondary element comprises a plurality of secondary elements, each projecting light reflecting from that area of interest to the detector in a way that produces a different response of the detector.

14. A method of measuring reflectivity of light from a surface exhibiting an evanescent wave phenomenon at total internal reflection, the method comprising:
a) reflecting light from a plurality of sensing areas of interest which exhibit the evanescent wave phenomenon, arranged one-dimensionally on a surface, over a range of angles of incidence for each area, one or more of the sensing areas of interest being capable of binding to material in a fluid sample that comes in contact with them;
b) projecting an image of the surface to a plurality of secondary optical elements, with sufficiently sharp focus so that light reflected from different sensing areas of interest is projected to substantially different secondary elements;
c) projecting the light from the secondary elements to a detector sufficiently close to a focal plane of the secondary elements so that light reflected from each sensing area of interest at different angles of incidence within its range of angles is spread out to sufficiently different locations on reaching the detector to distinguish the detector response for the different angles of incidence; and
d) determining, from a response of the detector, how much light is reflected from each sensing area of interest, as a function of angle of incidence over the range of angles for that area, for at least one time interval.

15. A method according to claim 14, also comprising passing one or more fluid samples over the plurality of sensing areas of interest, the fluid samples containing at least one material which binds to at least one of the sensing areas of interest, changing how much light is reflected from that sensing area of interest, as a function of angle of incidence over the range of angles for that area.

16. A method according to claim 15, also comprising analyzing response data from the detector to determine one or more of a presence, a concentration, a binding rate of the material in the one or more samples to the sample surface, and a dissociation rate of the material in the one or more samples from the sample surface.

17. A method according to claim 15, wherein passing one or more fluid samples comprises passing a fluid sample over at least one sensing area of interest that does not bind to the material, and analyzing the response data of the detector comprises comparing the response data from light reflecting from the area that binds to the material, to the response data from light reflecting from the area that does not bind to the material.

18. A method according to claim 14, wherein determining, from a response of the detector, how much light is reflected from each sensing area of interest comprises combining response data from light reflecting from neighboring sensing areas of interest.

19. A method according to claim 14, wherein determining, from a response of the detector, how much light is reflected from each sensing area of interest comprises combining response data from light projected onto the detector at neighboring locations.

* * * * *